US010201622B2

(12) United States Patent
Loadman et al.

(10) Patent No.: US 10,201,622 B2
(45) Date of Patent: Feb. 12, 2019

(54) TUMOUR-TARGETED THERANOSTIC

(71) Applicants: University of Bradford, Yorkshire (GB); The Trustees of The Leland Stanford Junior University, Palo Alto, CA (US)

(72) Inventors: Paul Loadman, Bradford (GB); Robert Falconer, Bradford (GB); Jason Gill, Bradford (GB); Jianghong Rao, Stanford, CA (US); Heike E. Daldrup-Link, Stanford, CA (US)

(73) Assignees: The Trustees of The Leland Stanford Junior University, Palo Alto, CA (US); Incanthera Ltd, Manchester (GB)

( * ) Notice: Subject to any disclaimer, the term of this patent is extended or adjusted under 35 U.S.C. 154(b) by 72 days.

(21) Appl. No.: 14/908,096

(22) PCT Filed: Jul. 25, 2014

(86) PCT No.: PCT/EP2014/066087
§ 371 (c)(1),
(2) Date: Jan. 27, 2016

(87) PCT Pub. No.: WO2015/014756
PCT Pub. Date: Feb. 5, 2015

(65) Prior Publication Data
US 2016/0303257 A1 Oct. 20, 2016

(30) Foreign Application Priority Data

Aug. 2, 2013 (GB) .................................. 1313900.1

(51) Int. Cl.
| | | |
|---|---|---|
| *A61K 51/00* | (2006.01) | |
| *A61M 36/14* | (2006.01) | |
| *A61K 49/18* | (2006.01) | |
| *A61K 31/165* | (2006.01) | |
| *A61K 49/08* | (2006.01) | |
| *A61K 47/65* | (2017.01) | |
| *A61K 47/60* | (2017.01) | |
| *A61K 47/69* | (2017.01) | |

(52) U.S. Cl.
CPC ........ *A61K 49/1866* (2013.01); *A61K 31/165* (2013.01); *A61K 47/60* (2017.08); *A61K 47/65* (2017.08); *A61K 47/6927* (2017.08); *A61K 47/6929* (2017.08); *A61K 49/085* (2013.01); *A61K 49/186* (2013.01)

(58) Field of Classification Search
CPC .... A61K 49/1866; A61K 49/00; A61K 47/00; A61K 47/6929; A61K 47/6927; A61K 47/65; A61K 47/60; A61K 31/00; A61K 31/165; A61K 49/085; A61K 49/08; A61K 49/186
USPC .............. 424/1.11, 1.65, 1.69, 9.1, 9.3, 9.32, 424/9.322, 9.323, 9.34, 9.36; 514/1, 1.1, 514/19.2, 19.3, 19.4, 19.5, 19.6, 20.1, 514/21.8, 21.9; 530/300, 329, 330; 997/700, 773
See application file for complete search history.

(56) References Cited

U.S. PATENT DOCUMENTS

| | | | | |
|---|---|---|---|---|
| 8,691,751 | B2 * | 4/2014 | Gill .......................... | C07K 7/06 514/1.3 |
| 8,927,486 | B2 * | 1/2015 | Falconer .......... | A61K 47/48338 514/1.3 |
| 9,358,303 | B2 * | 6/2016 | Gill .......................... | C07K 7/06 |
| 9,937,267 | B2 * | 4/2018 | Falconer .................. | C07K 7/06 |
| 9,956,296 | B2 * | 5/2018 | Gill .......................... | C07K 7/06 |
| 2003/0195152 | A1 | 10/2003 | Suarato et al. | |
| 2006/0074008 | A1 | 4/2006 | Senter et al. | |
| 2007/0117133 | A1 | 5/2007 | Trieu et al. | |
| 2009/0269284 | A1 | 10/2009 | Schultz Sikma et al. | |
| 2011/0275554 | A1 | 11/2011 | Falconer et al. | |
| 2016/0243252 | A1 | 8/2016 | Gill et al. | |

FOREIGN PATENT DOCUMENTS

| | | |
|---|---|---|
| EP | 1862470 A1 | 12/2007 |
| WO | WO-01/068145 A2 | 9/2001 |
| WO | WO-01/068145 A3 | 9/2001 |
| WO | WO-02/072620 A1 | 9/2002 |
| WO | WO-2005/023314 A1 | 3/2005 |
| WO | WO-2006/079120 A2 | 7/2006 |
| WO | WO-2006/079120 A3 | 7/2006 |
| WO | WO-2006/090813 A1 | 8/2006 |
| WO | WO-2006/110476 A2 | 10/2006 |
| WO | WO-2006/110476 A3 | 10/2006 |
| WO | WO-2008/125800 A2 | 10/2008 |
| WO | WO-2008/125800 A3 | 10/2008 |
| WO | WO-2010/046628 A1 | 4/2010 |
| WO | WO-2015/014756 A1 | 2/2015 |

OTHER PUBLICATIONS

Ansari et al, Small, 2014, vol. 10, No. 3, pp. 566-575.*

(Continued)

*Primary Examiner* — D. L. Jones
(74) *Attorney, Agent, or Firm* — Mintz Levin Cohn Ferris Glovsky and Popeo, P.C.; Muriel Liberto, Esq.

(57) ABSTRACT

The present inventors have harnessed the targeting of nanoparticles to tumor sites, combined with the tumor site specific elevated MMP-14 activity within one conjugate to simultaneously deliver a vascular disrupting agent (VDA) and a MRI contrast agent to a tumor site. The MMP activatable conjugate of the present invention provides both therapeutic and diagnostic functions—and is referred to as a "theranostic". The theranostic conjugate of the present invention achieves the benefits of tumor site specificity, VDA delivery and MRI contrast agent delivery in a single theranostic conjugate. Consequently, the present invention provides a cancer "theranostic" which improves therapeutic efficacy while simultaneously reducing dose-limiting systemic toxicities and provides a tool for rapidly and non-invasively identifying tumor location, monitoring drug delivery and pharmacodynamics.

18 Claims, 10 Drawing Sheets

Specification includes a Sequence Listing.

(56) References Cited

OTHER PUBLICATIONS

Poster Presentation P819, Sep. 10, 2011, Development of a Novel Activatable Theragnostic Superparamagnetic Iron oxide Nanoparticle, 2 pages.*
International Search Report issued in PCT/EP2014/066087 dated Oct. 9, 2014.
J. M. Atkinson et al. "Development of a Novel Tumor-Targeted Vasular Disrupting Agent Activated by Membrane-Type Matrix metalloproteinases", Cancer Resarch, vol. 70, No. 17, Jul. 27, 2010, pp. 6902-6912, XP055142175.
Celina Ansari et al. "Development of Novel Tumor-Targeted Theranostic Nanoparticles Activated by Membrane-Type Matrix Metalloproteinases for Combined Cancer Magnetic Resonance Imaging and therapy", SMALL, vol. 10, No. 3, Aug. 27, 2013, pp. 566-575, XP055142050.
Jason H. Gill et al. "Tumor-Targeted Prodrug ICT2588 Demonstrates Therapeutic Activity against Solid Tumors and Reduced Potential for Cardiovascular Toxicity", Molecular Pharmaceutics, vol. 11, No. 4, Dec. 9, 2013, pp. 1294-1300, XP055141934.
Ansari C. et al.: "Development of a Novel activatable Theranostic Superparamagnetic Iron Oxide Nanoparticle", Sep. 10, 2011, XP055141916.
Tina Lam et al. "Superparamagnetic ironoxide based nanoprobes for imaging and theranostics", Advances in Colloid and Interface Science, vol. 199-200, Jul. 5, 2013, pp. 95-113, XP055141938.
Ralph P. Mason et al. "A perspective on vascular disrupting agents that interact with tubulin: preclinical tumor imaging and biological assessment", Integrative Biology, vol. 3, No. 4, Jan. 1, 2011, p. 375, XP055142034.
"Abnormal Hemoglobins." *Biochemistry*. Voet et al., eds. New York: John Wiley & Sons, Inc. (1995):235-241.
Aitkhozhina et al. "10-Amino Analogs of Colchicine: Synthesis, Structure, and Biological Activity." *Bioorganicheskaia Khimia*. 22.5(1996):383-386. (Russian Original and English Abstract).
Albright et al. "Matrix-Metalloproteinase-Activated Doxorubicin Prodrugs Inhibit HT1080 Zenograft Growth Better than Doxorubicin with Less Toxicity." *Mol. Cancer Therapeutics*. 4. 5(2005):751-760.
"Analog." On-line Medical Dictionary. Mar. 5, 2000. Web. Jul. 7, 2005. http://cancerweb.ncl.ac.uk/cgi-bin/omd?query=analog, 1 page.
Atkinson, J.M. et al. (Sep. 1, 2010, e-published Jul. 27, 2010). "Development of a novel tumor-targeted vascular disrupting agent activated by membrane-type matrix metalloproteinases," *Cancer Res* 70(17):6902-6912.
Beerepoot et al. "Phase I Clinical Evaluation of Weekly Administration of the Novel Vascular-Targeting Agent, ZD6126, in Patients with Solid Tumors." *J. Clin. Oncol*. 24.10(2006):1491-1498.
Berendsen et al. "A Glimpse of the Holy Grail?" *Science*. 282. 5389(1998):642-643.
Bradley et al. "Limits of Cooperativity in a Structurally Modular Protein: Response of the Notch Ankyrin Domain to Analogous Alanine Substitutions in Each Repeat." *J. Mol. Biol*. 324(2002):373-386.
Chau et al. "Synthesis and Characterization of Dextran-Peptide-Methotrexate Conjugates for Tumor Targeting via Mediation by Matrix Metalloproteinase II and Matrix Metalloproteinase IX." *Bioconj. Chem*. 15.4(2004):931-941.
Chaudhuri et al. "The Interaction of the B-ring of Colchicine with α-Tubulin: A Novel Footprinting Approach." *J. Mol. Biol*. 303. 5(2000):679-692.
Davis et al. "ZD6126: A Novel Vascular-Targeting Agent that Causes Selective Destruction of Tumor Vasculature." *Cancer Res*. 62.24(2002):7247-7253.
Denekamp. "Endothelial Cell Proliferation as a Novel Approach to Targeting Tumour Therapy." *Br. J. Cancer*. 45(1982):136-139.
"Derivative." On-line Medical Dictionary. Nov. 18, 1997. Web. Jul. 7, 2005. http://cancerweb.ncl.ac.uk/cgi-bin/omd?query=derivative, 1 page.
"Designing Custom Peptides." Sigma Genosys. Web. Dec. 16, 2004. http://www.sigma-genosys.com/peptide_design.asp, 2 pages.
Dubowchik et al. "Receptor-Mediated and Enzyme-Dependent Targeting of Cytotoxic Anticancer Drugs." *Pharmacol. Therapeutics*. 83(1999):67-123.
Egeblad, M. et al. (Mar. 2002). "New functions for the matrix metalloproteinases in cancer progression," *Nat Rev Cancer* 2(3):161-174.
Esbolaev et al. "C-10 Amino Acid Derivatives of Colchicine." *Chem. Nat. Compounds*. 28.3-4(1992):325-328.
Esbolaev et al. "C-10 Dipeptide Derivatives of Colchicine." *Khimiya Prirodnykh Soedinenii*. 1(1989):91-95. (Russian Original and English Abstract).
Esbolaev et al. "Cytotoxic Activity of Dipeptide Derivatives of Colchicine." *Izvestiya Akademii Nauk Kazakhskoi SSR*. 5(1989):83-86. (Russian Original and English Abstract).
Hamel. "Antimitotic Natural Products and Their Interactions with Tubulin." *Med. Res. Rev*. 16.2(1996):207-231.
Hollebecque, A. et al. (May 2012). "Vascular disrupting agents: a delicate balance between efficacy and side effects," *Curr Opin Oncol* 24(3):305-315.
Hooper et al. "Identification and Development of Vascular Disrupting Agents: Natural Products That Interfere with Tumor Growth." *Natural Products and Cancer Drug Discovery*. Koehn, ed. New York: Springer Science. (2013):17-38.
Kline et al. "Novel Antitumor Prodrugs Designed for Activation by Matrix Metalloproteinases-2 and -9." *Mol. Pharma*. 1.1(2004):9-22.
Kratz et al. "Development and In Vitro Efficacy of Novel MMP2 and MMP9 Specific Doxorubicin Albumin Conjugates." Bioorg. Med. Chem.Lett. 11.15(2001):2001-2006.
Kratz et al. "Prodrugs of Anthracyclines in Cancer Chemotherapy." Curr. Med. Chem. 13.5(2006):477-523.
Lippert. "Vascular Disrupting Agents." *Bioorg. Med. Chem*. 15.2(2007):605-615.
Mansour et al. "A New Approach for the Treatment of Malignant Melanoma: Enhanced Antitumor Efficacy of an Albumin-Binding Doxorubicin Prodrug that is Cleaved by Matrix Metalloproteinase 2." *Cancer Res*. 63.14(2003):4062-4066.
"Matrix Metalloproteinases." *MMP*. (2007):1-15.
Nagase et al. "Human Matrix Metalloproteinase Specificity Studies using Collagen Sequence-Based Synthetic Peptides." *Biopolymers*. 40(1996):399-416.
Ngo et al. "Computational Complexity, Protein Structure Prediction, and the Levinthal Paradox." *The Protein Folding Problem and Tertiary Structure Production*. Merz, Jr., et al., eds. Boston: Birkhauser. (1994):491-506.
Quinn et al. "Toxicity Quantitative Structure—Activity Relationships of Colchicines." *J. Med. Chem*. 24.5(1981):636-639.
*Remington's Pharmaceutical Sciences*. Gennaro, ed. Easton, PA: Mack Publishing Co. (1985):1418.
Rudinger. "Characteristics of the Amino Acids as Components of a Peptide Hormone Sequence." *Peptide Hormones*. Parsons, ed. Baltimore, MD: University Park Press. (1976):1-7.
Rustin et al. "Phase I Clinical Trial of Weekly Combretastatin A4 Phosphate: Clinical and Pharmacokinetic Results." *J. Clin. Oncol*. 21.15(2003):2815-2822.
Siemann et al. "Differentiation and Definition of Vascular-Targeted Therapies." *Clin. Cancer Res*. 11(2005):416-420.
Tozer et al. "Disrupting Tumour Blood Vessels." *Nat. Rev. Cancer*. 5.6(2005):423-435.

* cited by examiner

SEQUENCE LISTING

```
<160> NUMBER OF SEQ ID NOS: 11

<210> SEQ ID NO 1
<211> LENGTH: 4
<212> TYPE: PRT
<213> ORGANISM: Homo sapiens
<220> FEATURE:
<221> NAME/KEY: X
<222> LOCATION: (2)..(2)
<223> OTHER INFORMATION: homophenylalanine

<400> SEQUENCE: 1

Gly Xaa Tyr Leu
1

<210> SEQ ID NO 2
<211> LENGTH: 6
<212> TYPE: PRT
<213> ORGANISM: Homo sapiens
<220> FEATURE:
<221> NAME/KEY: X
<222> LOCATION: (3)..(3)
<223> OTHER INFORMATION: citruline
<220> FEATURE:
<221> NAME/KEY: X
<222> LOCATION: (5)..(5)
<223> OTHER INFORMATION: homophenylalanine

<400> SEQUENCE: 2

Arg Ser Xaa Gly Xaa Tyr
1               5
```

```
<210> SEQ ID NO 3
<211> LENGTH: 5
<212> TYPE: PRT
<213> ORGANISM: Homo sapiens
<220> FEATURE:
<221> NAME/KEY: X
<222> LOCATION: (1)..(1)
<223> OTHER INFORMATION: citruline
<220> FEATURE:
<221> NAME/KEY: X
<222> LOCATION: (3)..(3)
<223> OTHER INFORMATION: homophenylalanine

<400> SEQUENCE: 3

Xaa Gly Xaa Tyr Leu
1               5

<210> SEQ ID NO 4
<211> LENGTH: 6
<212> TYPE: PRT
<213> ORGANISM: Homo sapiens
<220> FEATURE:
<221> NAME/KEY: x
<222> LOCATION: (2)..(2)
<223> OTHER INFORMATION: citruline
<220> FEATURE:
<221> NAME/KEY: x
<222> LOCATION: (4)..(4)
<223> OTHER INFORMATION: homophenylalanine

<400> SEQUENCE: 4

Ser Xaa Gly Xaa Tyr Leu
1               5

<210> SEQ ID NO 5
<211> LENGTH: 8
<212> TYPE: PRT
<213> ORGANISM: Homo sapiens
<220> FEATURE:
<221> NAME/KEY: x
<222> LOCATION: (1)..(1)
<223> OTHER INFORMATION: beta alanine
<220> FEATURE:
<221> NAME/KEY: x
<222> LOCATION: (5)..(5)
<223> OTHER INFORMATION: citruline
<220> FEATURE:
<221> NAME/KEY: x
<222> LOCATION: (7)..(7)
<223> OTHER INFORMATION: homophenylalanine

<400> SEQUENCE: 5

Xaa Cys Arg Ser Xaa Gly Xaa Tyr
1               5

<210> SEQ ID NO 6
<211> LENGTH: 7
<212> TYPE: PRT
<213> ORGANISM: Homo sapiens
<220> FEATURE:
<221> NAME/KEY: x
<222> LOCATION: (3)..(3)
<223> OTHER INFORMATION: citruline
<220> FEATURE:
<221> NAME/KEY: x
<222> LOCATION: (5)..(5)
<223> OTHER INFORMATION: homophenylalanine

<400> SEQUENCE: 6

Arg Ser Xaa Gly Xaa Tyr Leu
1               5
```

```
<210> SEQ ID NO 7
<211> LENGTH: 8
<212> TYPE: PRT
<213> ORGANISM: Homo sapiens
<220> FEATURE:
<221> NAME/KEY: x
<222> LOCATION: (4)..(4)
<223> OTHER INFORMATION: citruline
<220> FEATURE:
<221> NAME/KEY: x
<222> LOCATION: (5)..(5)
<223> OTHER INFORMATION: homophenylalanine
<220> FEATURE:
<221> NAME/KEY: misc_feature
<222> LOCATION: (6)..(6)
<223> OTHER INFORMATION: Xaa can be any naturally occurring amino acid

<400> SEQUENCE: 7

Cys Arg Ser Xaa Gly Xaa Tyr Leu
1               5

<210> SEQ ID NO 8
<211> LENGTH: 9
<212> TYPE: PRT
<213> ORGANISM: Homo sapiens
<220> FEATURE:
<221> NAME/KEY: x
<222> LOCATION: (1)..(1)
<223> OTHER INFORMATION: beta alanine
<220> FEATURE:
<221> NAME/KEY: x
<222> LOCATION: (5)..(5)
<223> OTHER INFORMATION: citruline
<220> FEATURE:
<221> NAME/KEY: x
<222> LOCATION: (7)..(7)
<223> OTHER INFORMATION: homophenylalanine

<400> SEQUENCE: 8

Xaa Cys Arg Ser Xaa Gly Xaa Tyr Leu
1               5

<210> SEQ ID NO 9
<211> LENGTH: 9
<212> TYPE: PRT
<213> ORGANISM: Homo sapiens
<220> FEATURE:
<221> NAME/KEY: x
<222> LOCATION: (1)..(1)
<223> OTHER INFORMATION: beta alanine
<220> FEATURE:
<221> NAME/KEY: x
<222> LOCATION: (4)..(4)
<223> OTHER INFORMATION: citruline
<220> FEATURE:
<221> NAME/KEY: x
<222> LOCATION: (6)..(6)
<223> OTHER INFORMATION: homophenylalanine

<400> SEQUENCE: 9

Xaa Arg Ser Xaa Gly Xaa Tyr Leu Cys
1               5

<210> SEQ ID NO 10
<211> LENGTH: 10
<212> TYPE: PRT
<213> ORGANISM: Homo sapiens
<220> FEATURE:
<221> NAME/KEY: x
<222> LOCATION: (1)..(1)
<223> OTHER INFORMATION: beta alanine
```

```
<220> FEATURE:
<221> NAME/KEY: x
<222> LOCATION: (4)..(4)
<223> OTHER INFORMATION: citruline
<220> FEATURE:
<221> NAME/KEY: x
<222> LOCATION: (6)..(6)
<223> OTHER INFORMATION: homophenylalanine

<400> SEQUENCE: 10

Xaa Arg Ser Xaa Gly Xaa Tyr Leu Tyr Cys
1               5                   10

<210> SEQ ID NO 11
<211> LENGTH: 10
<212> TYPE: PRT
<213> ORGANISM: Homo sapiens
<220> FEATURE:
<221> NAME/KEY: x
<222> LOCATION: (1)..(1)
<223> OTHER INFORMATION: beta alanine
<220> FEATURE:
<221> NAME/KEY: x
<222> LOCATION: (5)..(5)
<223> OTHER INFORMATION: cit
<220> FEATURE:
<221> NAME/KEY: x
<222> LOCATION: (7)..(7)
<223> OTHER INFORMATION: homophenylalanine

<400> SEQUENCE: 11

Xaa Cys Arg Ser Xaa Gly Xaa Tyr Leu Tyr
1               5                   10
```

TUMOUR-TARGETED THERANOSTIC

STATEMENT AS TO RIGHTS TO INVENTIONS MADE UNDER FEDERALLY SPONSORED RESEARCH AND DEVELOPMENT

This invention was made with Government support under contracts CA151459 and CA156124 awarded by the National Institutes of Health. The Government has certain rights in this invention.

RELATED APPLICATIONS

This application is a national stage application, filed under 35 U.S.C. § 371, of International Application No. PCT/EP2014/066087, filed on Jul. 25, 2014, which claims priority to GB Patent Application No. 1313900.1, filed on Aug. 2, 2013, the contents of which are hereby fully incorporated by reference.

SEQUENCE LISTING

The present application contains a sequence listing which has been submitted in ASCII format via EFS-Web and is hereby incorporated by reference in its entirety. The ASCII copy was created on Jun. 9, 2016, is named 41303-513N01US_ST25.txt and is 3.39 KB in size.

INTRODUCTION

Conventional cancer therapy involves radiation and cytotoxic chemotherapeutic treatment, both of which generate serious toxic side effects. Mechanistically these treatments do not exclusively target cancer cells, but also damage proliferating cell types of the digestive tract, central nervous system and bone marrow, and physiological functions of many tissues, commonly resulting in toxicities and impaired organ function. Furthermore conventional cancer therapy does not allow drug delivery, pharmacodynamics or therapeutic response to be monitored.

Matrix metalloproteinases (MMP) comprise a family of 24 zinc-dependent endopeptidases with structural similarity. The MMP family comprises two groups, that is, the soluble type and the membrane-type MMPs (MT-MMPs), with the MT-MMPs further subclassified by their cell surface association, either by a transmembrane domain (MT1, 2, 3, and 5) or by glycophosphatidylinositol anchor (MT4 and 6). Transmembrane MT-MMPs play a role in many tumourigenic processes, they facilitate tumour cell invasion and play a major role in controlling tumour cell growth, migration, differentiation, and ultimately metastasis. Transmembrane MT-MMPs expression, especially MT1-MMP (also known as MMP-14), is elevated in nearly all solid tumours. MMP-14 is overexpressed in all solid tumours which contain a vascular component.

The pivotal role for MMP-14 in tumour expansion and progression, its elevated expression in solid tumours and its unique localization tethered to the cell surface has been exploited in cancer therapy by Atkinson et al (Atkinson et al, Cancer Research 2010, 70, 6902) who demonstrated that a systemically non-toxic prodrug comprising an MMP-14 cleavable peptide conjugated to azademethylcolchicine, a highly potent vascular disrupting agent (VDA), was selectively activated by MMP-14 at the tumour site. Therefore the toxic VDA activity is targeted to the tumour site. This was exemplified by the prodrug ICT-2588.

Nanoparticles loaded with anti-tumour agents have been assessed as a strategy to deliver anti-tumour agents to tumour sites. Accumulation of nanoparticles occurs at tumour sites. This observation has been called the enhanced permeability and retention (EPR) effect. EPR is the retention at tumour sites, in preference to normal tissues, of macromolecules because tumour neovasculature is abnormal and "leaky". However, since extravasation may occur across organs of the reticuloendothelial system (RES) it has been recognised that strategies are required to ensure tumour-selective delivery of toxic agents to reduce the potential for toxic side effects in the RES.

MR probes for imaging cancer have been previously described. However, such probes lacked any anti-cancer activity.

Theranostic nanoparticles have been suggested. However these previous approaches have largely proved unsuccessful.

There remains a need to overcome previous shortcomings in cancer therapy.

SUMMARY OF THE INVENTION

The present inventors have harnessed the targeting of nanoparticles to tumour sites, combined with the tumour site specific elevated MMP-14 activity within one conjugate to simultaneously deliver a vascular disrupting agent (VDA) and a MRI contrast agent to a tumour site. The MMP activatable conjugate of the present invention provides both therapeutic and diagnostic functions—and is referred to as a "theranostic". The theranostic conjugate of the present invention achieves the benefits of tumour site specificity, VDA delivery and MRI contrast agent delivery in a single theranostic conjugate. Consequently, the present invention provides a cancer "theranostic" which improves therapeutic efficacy whilst simultaneously reducing dose-limiting systemic toxicities and provides a tool for rapidly and non-invasively identifying tumour location, monitoring drug delivery and pharmacodynamics.

The present invention provides a matrix metalloprotease (MMP) activatable conjugate comprising a vascular disrupting agent (VDA) which binds to the colchicine binding site of tubulin, a MMP cleavable peptide comprising the amino acid sequence -Gly-Hof-Tyr-Leu- (SEQ ID NO: 1) or -Arg-Ser-Cit-Gly-Hof-Tyr- (SEQ ID NO: 2) and a nanoparticle bearing a magnetic resonance imaging (MRI) contrast agent. (Hof stands for homophenylalanine.)

The nanoparticle is a moiety of sufficient size to accumulate at a tumour site. Accumulation at tumour sites occurs because of the abnormal architecture of tumour vasculature allowing extravasation of macromolecules. Accumulation occurs at the tumour site due the EPR effect. The nanoparticle can be functionalised with an MRI contrast agent. The MRI contrast agent allows detection of the site of accumulation of the nanoparticle and hence the site of VDA delivery to a tumour.

The amino acid sequence -Gly-Hof-Tyr-Leu-(SEQ ID NO: 1) or -Arg-Ser-Cit-Gly-Hof-Tyr- (SEQ ID NO: 2) comprised within the MMP cleavable peptide means that the peptide is cleavable in the presence of MMP-14 which is over expressed in solid tumours. Preferably the MMP cleavable peptide is selectively cleavable by MMP-14. Therefore the conjugate is advantageously a MMP-14 activatable conjugate.

The VDA causes collapse of the tumour vasculature providing several advantages including tumour cell death.

In preferred embodiments the conjugate does not comprise folate. A folate moiety is not required for tumour specific targeting of the conjugate of the present invention and the absence of a folate moiety enhances tumour site targeting of the conjugate.

In embodiments the conjugate of the present invention comprises a MMP cleavable peptide which can comprise the amino acid sequence -Gly-Hof-Tyr-Leu- (SEQ ID NO: 1), optionally -Cit-Gly-Hof-Tyr-Leu- (SEQ ID NO: 3) (Cit stands for citruline) and further optionally -Ser-Cit-Gly-Hof-Tyr-Leu- (SEQ ID NO: 4). In embodiments the conjugate of the present invention comprises a MMP cleavable peptide which can comprise the amino acid sequence -Arg-Ser-Cit-Gly-Hof-Tyr- (SEQ ID NO: 2) or -βAla-Cys-Arg-Ser-Cit-Gly-Hof-Tyr (SEQ ID NO: 5). Beneficially, the MMP cleavable peptide may comprise an amino acid sequence -Arg-Ser-Cit-Gly-Hof-Tyr-Leu- (SEQ ID NO: 6).

The MMP cleavable peptide can further comprise an amino acid with a reactive group for conjugation to a nanoparticle or to a nanoparticle via a linker. A person skilled in the art would be aware of amino acids with a suitable side chain for conjugation. The MMP cleavable peptide can further comprise a -Cys-. Inclusion of a cysteine residue provides an —SH group which may be used for conjugation to the nanoparticle. An amino acid with a suitable side chain for conjugation may be included within the MMP cleavable peptide at a position that does not disrupt the MMP-14 recognition sequence -Gly-Hof-Tyr-Leu- (SEQ ID NO: 1) or -Arg-Ser-Cit-Gly-Hof-Tyr- (SEQ ID NO: 2). The MMP cleavable peptide can comprise -Cys-Arg-Ser-Cit-Gly-Hof-Tyr-Leu- (SEQ ID NO: 7). Further preferred sequences of the MMP cleavable peptide can include -βAla-Cys-Arg-Ser-Cit-Gly-Hof-Tyr-Leu- (SEQ ID NO: 8), -βAla-Arg-Ser-Cit-Gly-Hof-Tyr-Leu-Cys- (SEQ ID NO: 9) or -βAla-Arg-Ser-Cit-Gly-Hof-Tyr-Leu-Tyr-Cys- (SEQ ID NO: 10).

In embodiments the MMP cleavable peptide can be conjugated to the nanoparticle or to the nanoparticle via a linker at -βAla-.

The MMP cleavable peptide can be prepared using standard peptide synthesis techniques.

Generally, the MMP cleavable peptide in the conjugate of the present invention has an amino acid sequence of from four to about fifteen amino acids, optionally from six to twelve amino acids and further optionally eight, nine, ten or eleven amino acids.

In embodiments the peptide may further comprise an endcap to prevent non-specific exopeptidase cleavage of the MMP cleavable peptide. The endcap may be an N-terminal endcap. The endcap may be any organic moiety suitable for prevention of non-specific exopeptidase cleavage. In preferred embodiments the endcap may be fluorescein or FITC. In other embodiments conjugation of the MMP cleavable peptide to the nanoparticle may be via its terminal amino acid and may replace an endcap.

The MMP cleavable peptide in the conjugate of the present invention is preferably cleavable by MMP-14. Advantageously the MMP cleavable peptide of the present invention is selectively cleavable by MMP-14. Therefore in embodiments the MMP cleavable peptide is not cleavable, or only very slowly cleavable, by other MMPs. MMP-14 is overexpressed in tumour vasculature and therefore is present and overexpressed in all solid tumours which contain a vascular component. Consequently, overexpression of MMP-14 is found at a wider range of solid tumour sites than the targeting moieties which have been used in other tumour pro-drugs. Furthermore, MMP-14 is also overexpressed in many solid tumours themselves.

The conjugate of the present invention is non-toxic prior to contacting MMP-14 since the action of MMP-14 is needed to release the VDA. The conjugated VDA is non-toxic in normal tissues because they lack high MMP-14 activity. Therefore systemic toxicity is avoided. A benefit of conjugates of the present invention is that the activation is "built-in" and does not require external stimuli for release of the VDA. The conjugate instead relies on tumour-associated MMP-14 activation.

The nanoparticle of the conjugate of the present invention is a macromolecule of sufficient size such that extravasation can occur from tumour vasculature. The nanoparticle should ideally have sufficient size to be able to penetrate the size of gap junction between leaky tumour vasculature and/or be sufficiently large to prevent rapid leakage into blood capillaries and/or be sufficiently large so that it is not cleared too quickly by the kidneys. Additionally the nanoparticle should ideally be small enough to escape capture by macrophages in the reticuloendothelial system in the liver and spleen and/or be small enough so that the kidneys are capable of clearing the nanoparticle.

The MMP activatable conjugate of the present invention may be referred to as a theranostic nanoparticle (TNP).

Nanoparticles may be classified by size and a diameter may be useful. In embodiments of the present invention nanoparticles can be 1 to 250 nm in diameter and preferably in the range of 3 to 200 nm in diameter. Alternatively, the nanoparticles can be in the size range from 3 to 160 nm or from 3 to 100 nm in diameter.

The nanoparticle of the present invention bears the MRI contrast agent which may be integral with the nanoparticle or linked to it. In embodiments of the present invention the MRI contrast agent can be part of a macromolecule and function as the nanoparticle.

The MRI contrast agent in the conjugate of the present invention may be selected from a transition metal ion or lanthanide metal ion. Suitable ions include those of gadolinium, iron, platinum, manganese, copper, gold, or barium. Optionally the MRI contrast agent is selected from iron oxides, magnetite ($Fe_3O_4$) or maghemite ($Fe_2O_3$). Commonly, iron oxide is used which in embodiments may be selected from superparamagnetic iron oxide (SPIO) or ultrasmall superparamagnetic iron oxide (USPIO).

In embodiments the nanoparticle features an organic or inorganic surface coating, which may be a natural or synthetic polymer. The coating may be selected from gelatin, dextran, casein, chitosan, PEG, polyvinylpyrrolidone (PVP), polyvinyl alcohol (PVA), or polyacrylic acid (PAA). In embodiments the nanoparticle contains a carbohydrate coating optionally dextran. In certain embodiments the nanoparticle bearing a MRI contrast agent is a dextran-coated iron oxide nanoparticle, preferably ferumoxytol. Ferumoxytol is a macromolecule and therefore provides both the MRI contrast agent and the nanoparticle in conjugates of the present invention.

The nanoparticle bearing the MRI contrast agent has suitable properties for the imaging mechanism, is compatible with biological systems and comprises moieties for conjugation. Conjugation of the nanoparticle, or the nanoparticle via a linking moiety, to the MMP cleavable peptide may be achieved by standard chemistry.

The VDA in the conjugate of the present invention is conjugated to the MMP cleavable peptide such that its toxic activity is masked until cleavage of the MMP cleavable peptide. Preferably the VDA is amenable to conjugation with an amino acid. Conjugation of the VDA to the MMP cleavable peptide may be achieved by standard chemistry.

Generally VDAs of the present invention are compounds which directly interact with tubulin, at the colchicine binding site, and consequently intracellular microtubules, resulting in a cytostatic or cytotoxic effect. This effect can stem from a VDA's ability to hinder tubulin polymerisation or depolymerisation.

In some embodiments of the conjugate of the present invention the VDA interacting with the colchicine binding site of tubulin can optionally be is selected from colchicine, colchicine analogs and derivatives, colchicinoids, combrestatins, phenstatin, podophyllotoxins, steganacins, amphethinile or stilbenes.

In some embodiments of the present invention the VDA is a colchicine analog or derivative and optionally may be selected from the group consisting of azademethylcolchicine, azacolchicine, N-methyl desacetylcolchicine, desacetylcolchicine and N-acetylcolchinol-O-phosphate. More preferably the VDA is azademethylcolchicine.

Use of VDAs, such as azademethylcolchicine, in the conjugate of the present invention offers further advantages in that VDAs can target tumour endothelia and so cause direct damage to the vasculature resulting in vessel collapse and a cessation of blood flow to the tumour and can be highly effective without needing to penetrate throughout the tumour mass.

The matrix metalloprotease (MMP) activatable conjugate of the present invention is targeted to and only activated at a tumour site because it has an MMP cleavable peptide comprising the amino acid sequence -Gly-Hof-Tyr-Leu- (SEQ ID NO: 1) or -Arg-Ser-Cit-Gly-Hof-Tyr- (SEQ ID NO: 2). Preferably the MMP cleavable peptide is a MMP-14 specifically cleavable peptide. The VDA, when released from the conjugate by cleavage of the MMP cleavable peptide at the tumour site, has its effect and can cause collapse of tumour vasculature. In one theory the nanoparticle assists in the tumour targeting and tumour site accumulation of the conjugate of the present invention. In an alternative theory the nanoparticle extravasates after cleavage of the MMP cleavable peptide and accumulates at the tumour site. Vascular collapse further ensures the nanoparticle remains at the tumour site. The conjugate has no further targeting moiety(ies). In particular the conjugate of the present invention does not comprise folate. No further targeting moiety(ies) is(are) required and, if present, could reduce the efficacy of the conjugate of the present invention.

An earlier study considered tumour-specific MR imaging and therapy via folate-conjugated nanoparticles, which were linked to a C- and N-terminal modified peptide conjugate of azademethylcolchicine which could be activated by MMPs (Ansari et al 2011). The conjugate of the present invention has several advantages over this folate-conjugated nanoparticle.

Folate receptors are overexpressed in developing or rapidly growing or dividing tissues in the body and therefore folate receptors are present at high levels in many non-tumourous tissues. Use of a folate targeting moiety may cause a folate-conjugated nanoparticle to be directed to rapidly growing or dividing normal tissues. Beneficially a specifically MMP-14 cleavable peptide would prevent azademethylcolchicine toxicity in non-tumour tissues, however the presence of a folate moiety may cause the MR imaging to detect tissues away from the tumour site. Folate receptors are present in a wide range of solid tumours, however this range of solid tumours is a subset of the solid tumour types overexpressing MMP-14. Reliance on a folate targeting moiety may therefore reduce the number of tumours in which such a therapy may be beneficial in comparison with use of a specifically MMP-14 cleavable peptide for targeting. Additionally the MMP cleavable conjugate of the present invention is simpler to manufacture than the previously considered folate-conjugated nanoparticles.

An embodiment of the present invention provides a matrix metalloprotease (MMP) activatable conjugate comprising: a VDA which binds to the colchicine binding site of tubulin selected from azademethylcolchicine, azacolchicine, N-methyl desacetylcolchicine, Desacetylcolchicine, N-acetylcolchinol-O-phosphate, a MMP cleavable peptide comprising an amino acid sequence -Arg-Ser-Cit-Gly-Hof-Tyr-Leu- (SEQ ID NO: 6), a nanoparticle of 3 to 200 nm in diameter bearing a magnetic resonance imaging (MRI) contrast agent, and wherein the conjugate does not comprise folate.

A further embodiment of the present invention provides a theranostic conjugate comprising a VDA which is a colchicine derivative, and preferably is azademethylcolchicine. The MMP cleavable peptide comprises -Arg-Ser-Cit-Gly-Hof-Tyr-Leu- (SEQ ID NO: 6) and can further comprise -Cys- as this may provide a functional group for attachment to other moieties of the conjugate so that the MMP cleavable peptide comprises -Cys-Arg-Ser-Cit-Gly-Hof-Tyr-Leu- (SEQ ID NO: 7). The theranostic conjugate also comprises a carbohydrate coated iron oxide nanoparticle, preferably ferumoxytol, as the nanoparticle bearing a MRI contrast agent. The theranostic conjugate requires no further targeting moiety. In particular the theranostic conjugate does not comprise a folate moiety.

Another aspect of the present invention provides a pharmaceutical composition comprising the conjugate of the present invention and a pharmaceutically acceptable carrier, vehicle, diluent or excipient.

The conjugate of the present invention and/or a pharmaceutical composition of the present invention can be administered by injection. Injection of the conjugate of the present invention may be via any suitable route, for example intravenous injection.

A further aspect provides the conjugate of the present invention, or the pharmaceutical composition described above, for use in therapy.

The present invention provides the conjugate of the present invention for use in treating cancer. Generally the cancer is a solid tumour. The solid tumour may be a sarcoma, a carcinoma, or a lymphoma. The conjugate of the present invention is for use in a method of treating a solid tumour comprising a vascular component.

The present invention provides the conjugate described above for use in a method for obtaining tumour site location information. The conjugate of the present invention can be used in a method for obtaining a MR image showing a tumour site.

The present invention provides the conjugate described above for use in a method of treating and imaging a tumour, the method comprising administering the conjugate to a subject and obtaining an MRI image of the subject's tumour site.

The present invention also provides the conjugate described above for use in a method of treating a tumour and monitoring VDA delivery to a tumour site, the method comprising administering the conjugate to a subject and obtaining one or more MRI images of the subject's tumour site, thereby monitoring VDA delivery to the tumour site. Optionally a first MRI image of the tumour site is obtained at a first point in time and a second MRI image of the tumour site is obtained at a subsequent second point in time, thereby enabling VDA delivery to the tumour site to be monitored.

This invention also provides a method for treating a tumour comprising administering to a subject in need thereof an effective amount of the conjugate of the present invention, the method can further comprise obtaining an MRI image of the subject's tumour site.

This invention also provides a method for treating and imaging a tumour comprising administering to a subject in need thereof an effective amount of a conjugate of the present invention and using MRI to image the tumour site.

This invention also provides a method for treating a tumour and monitoring VDA delivery to the tumour in a subject, the method comprising administering the conjugate to a subject in need thereof and obtaining one or more MRI images of the subject's tumour site. Optionally, a first MRI image of the tumour site is obtained at a first point in time and a second MRI image of the tumour site is obtained at a subsequent second point in time, thereby enabling VDA delivery to the tumour site to be monitored.

BRIEF DESCRIPTION OF THE DRAWINGS

FIG. 1 (B) shows synthesis of the theranostic nanoparticles. (ICT=MMP cleavable peptide-conjugated azademethylcolchicine)

FIG. 2 (B) shows a representative transmission electron microscopy image of CLIO-ICT. Inset shows crystalline iron oxide core of a single nanoparticle;

FIG. 2 (C) CLIO-ICT activation by MMP-14 in PBS buffer analysed by HPLC. Mass spectrum of the indicated peak confirmed the presence of product of TNP cleavage by MMP-14.

FIG. 3 (B) shows qPCR of MMP-14 expression of MMTV-PyMT, 4T1 and human dermal fibroblasts.

FIG. 3 (C) shows PyMT tumour sizes were measured daily for 7 days after intravenous injection of PBS, Ferumoxytol, CLIO-ICT and ICT. The tumour size increases in that of the PBS and Ferumoxytol administered subjects and decreases in the CLIO-ICT and ICT cases.

FIG. 4 (B) shows MR signal enhancement data in tumours corresponding to FIG. 4 quantified as $\Delta R_2=(R_2pre-R_2post)$.

Data are displayed as mean data of n=6 tumours in each group for 1 h and 24h time points.

Figure 5:
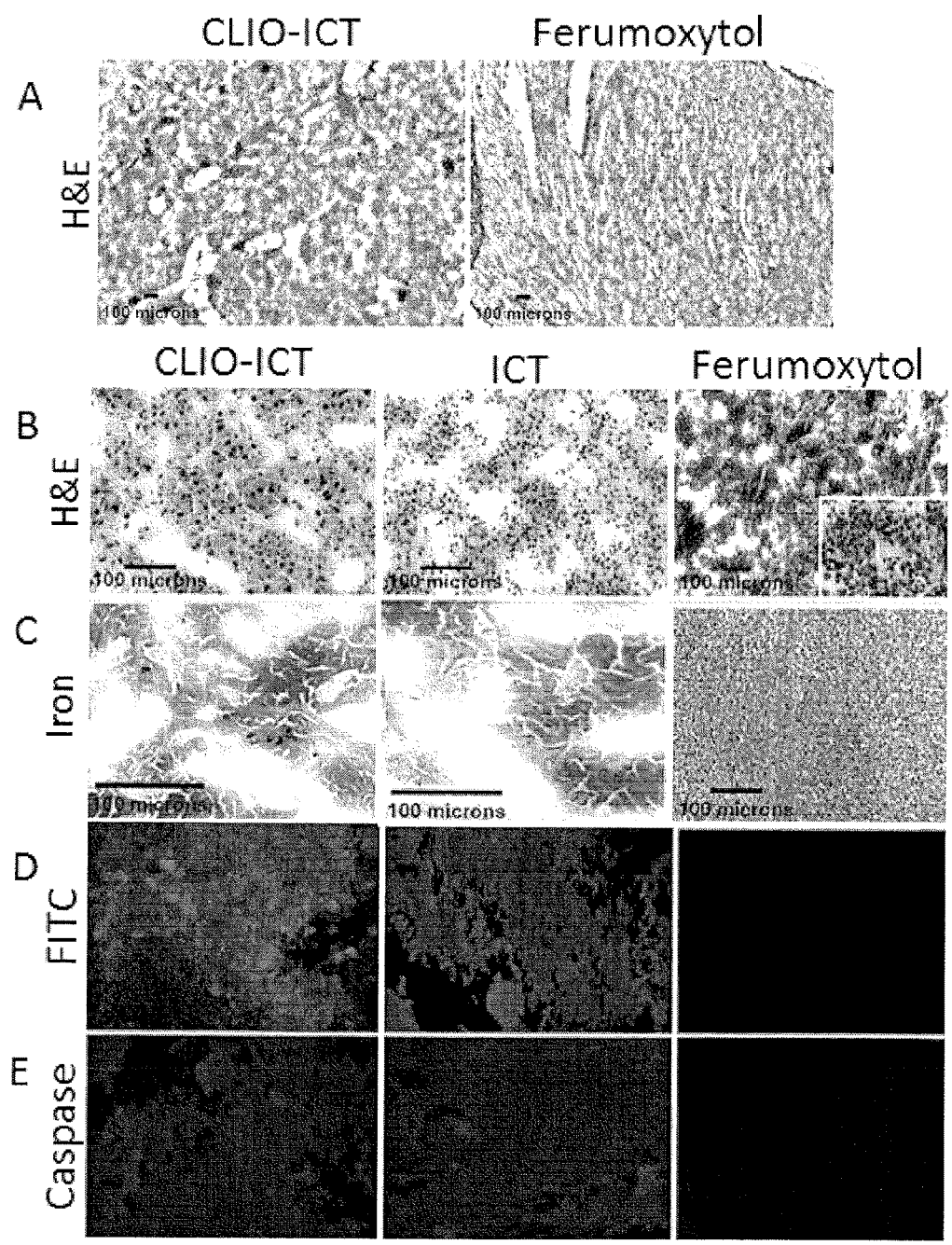

FIG. 5 (A) shows MMP-14 negative fibroblasts: H&E stained histologic sections of fibroblasts treated with CLIO-ICT and ICT showing no necrosis (both images taken at 40× magnification)

FIG. 5 (B) shows TNP-induced cell death in MMTV-PyMT tumours. H&E panels: CLIO-ICT treated tumour demonstrating diffuse necrosis (200× magnification); ICT treated tumour with predominately viable tumour cells and a subset of cells undergoing necrosis (200× magnification); Ferumoxytol treated tumour with diffuse viability and no necrosis (100× magnification, inset: 400× magnification).

FIG. 5 (C) shows iron panels: Scattered CLIO-ICT treated tumour and rare admixed histiocytes contain blue pigment indicating cytoplasmic iron deposition (200× magnification); ICT treated tumour shows no cytoplasmic iron deposition, scattered iron laden histiocytes serve as an internal positive control (200× magnification); Ferumoxytol treated tumour show cytoplasmic iron deposition, scattered iron laden histiocytiocytes serve as an internal positive control (200× magnification).

FIG. 5 (D) shows fluorescence microscopy showing FITC signal for CLIO-ICT and ICT but no signal for Ferumoxytol FIG. 5 (E) shows caspase-3 panels: CLIO-ICT and ICT treated tumours show Cy3 labeling throughout the samples; Ferumoxytol treated tumour shows few areas with weak Cy3 fluorescence (4× magnification).

Figure 6:
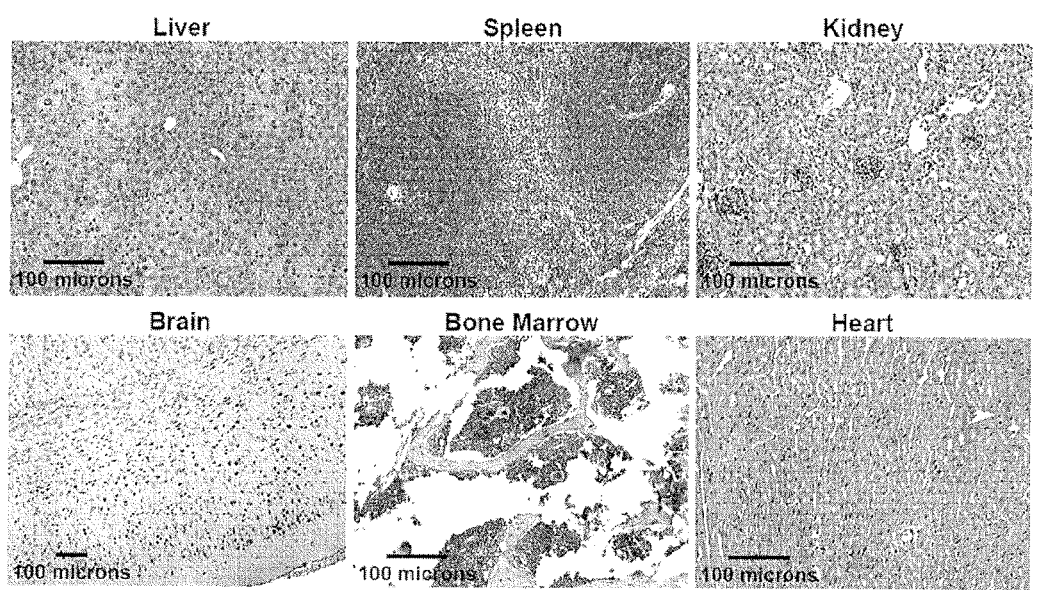

FIG. 6 shows CLIO-ICTs do not cause toxic effects in normal organs. Above histopathologies show no significant necrosis of normal organs on H&E staining of the A) Heart, B) Kidney, C) Spleen, D) Brain, E) Bone Marrow and F) Liver.

Figure 1:
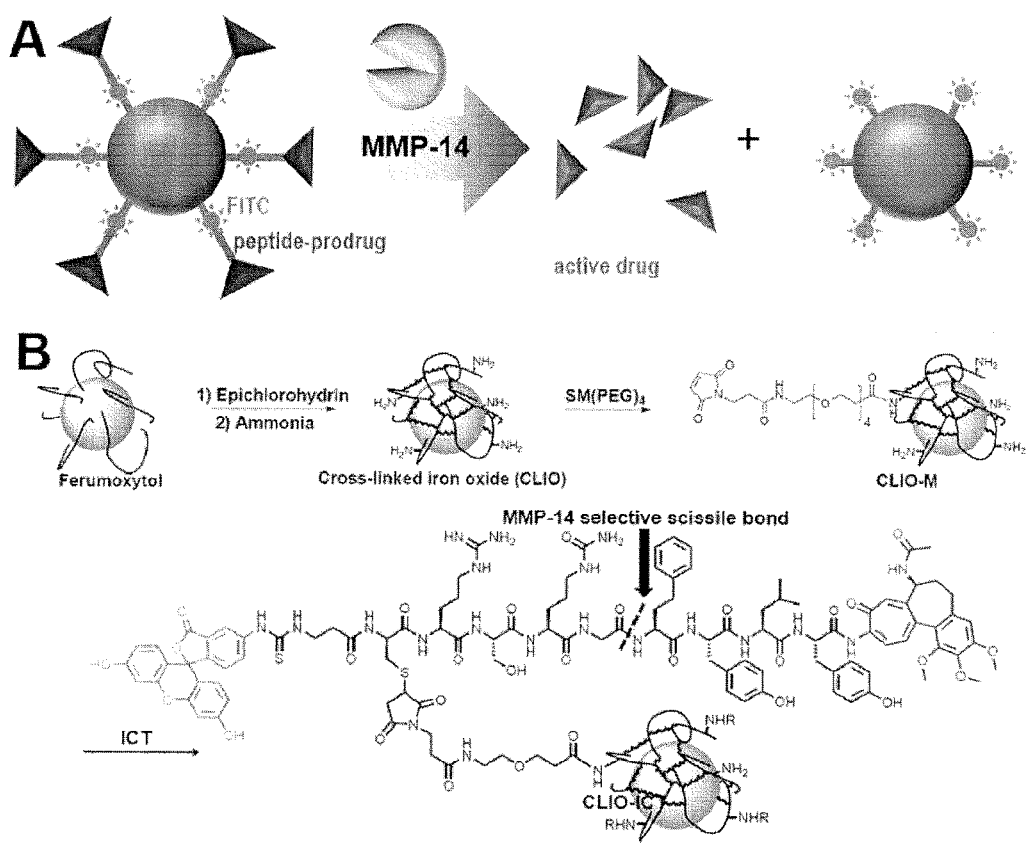
FIG. 1 (A) shows a schematic representation of a conjugate of the present invention activated by MMP-14. In this embodiment the nanoparticle bearing a MRI contrast agent is a nanoparticle with iron oxide core and is shown as a sphere, the MMP cleavable peptide is shown as bars and the VDA is shown as pyramids.
Figure 7:
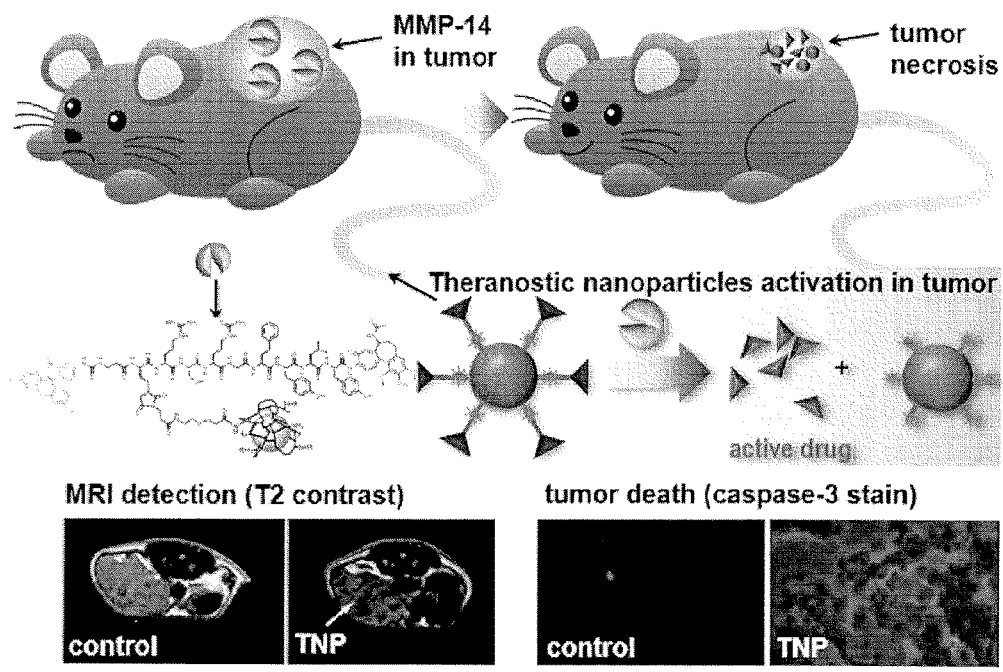

FIG. 7 schematically shows a summary of invention (see FIGS. 1 (A) and 1 (B))

Figure 8:
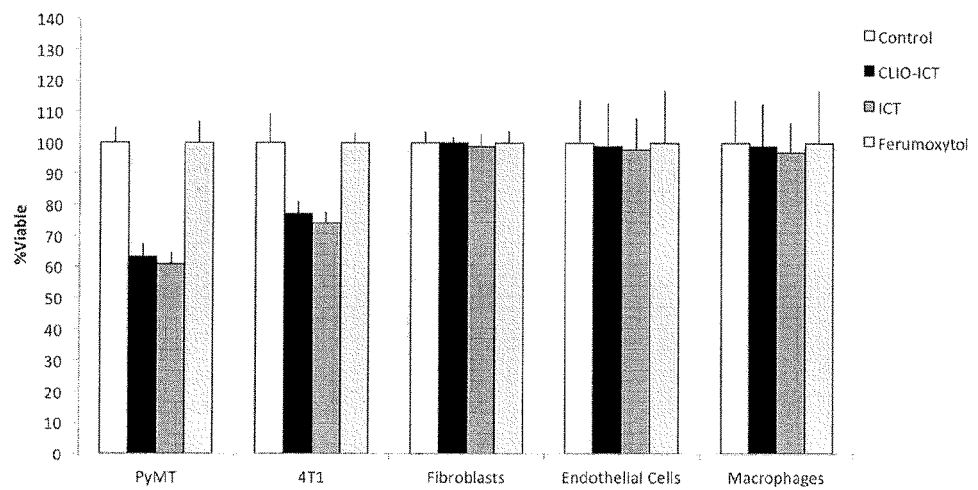

FIG. 8 shows selective cytotoxicity of CLIO-ICT and ICT against MMP-14 expressing cell types.

Figure 9:
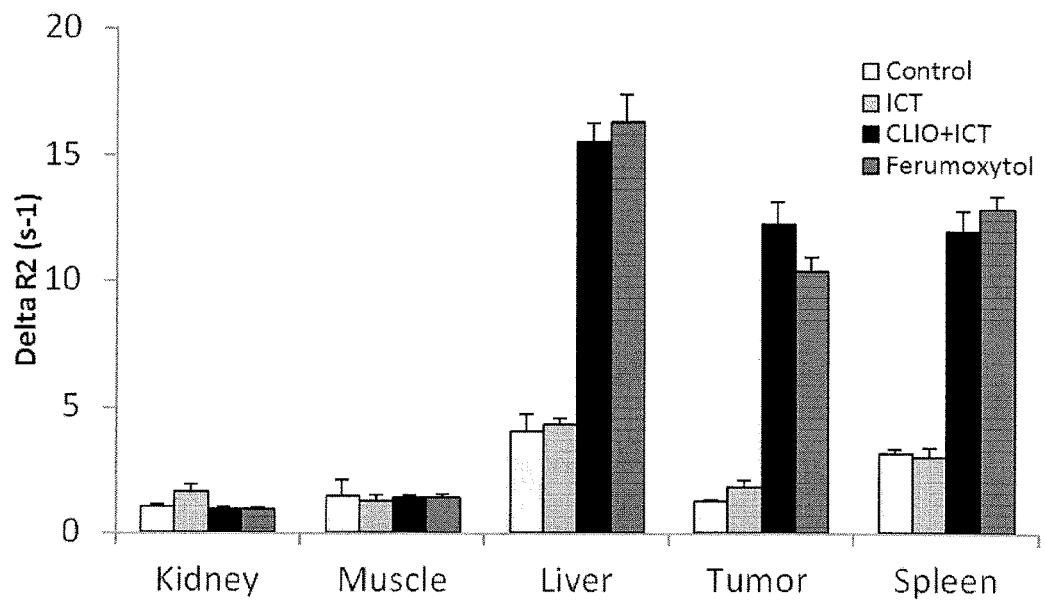

FIG. 9 shows accumulation of control, ICT, CLIO-ICT and ferumoxytol in accessory organs and tumour. Marked signal enhancement in RES organs—liver and spleen and no significant enhancement in the kidney or muscle.

Figure 10:
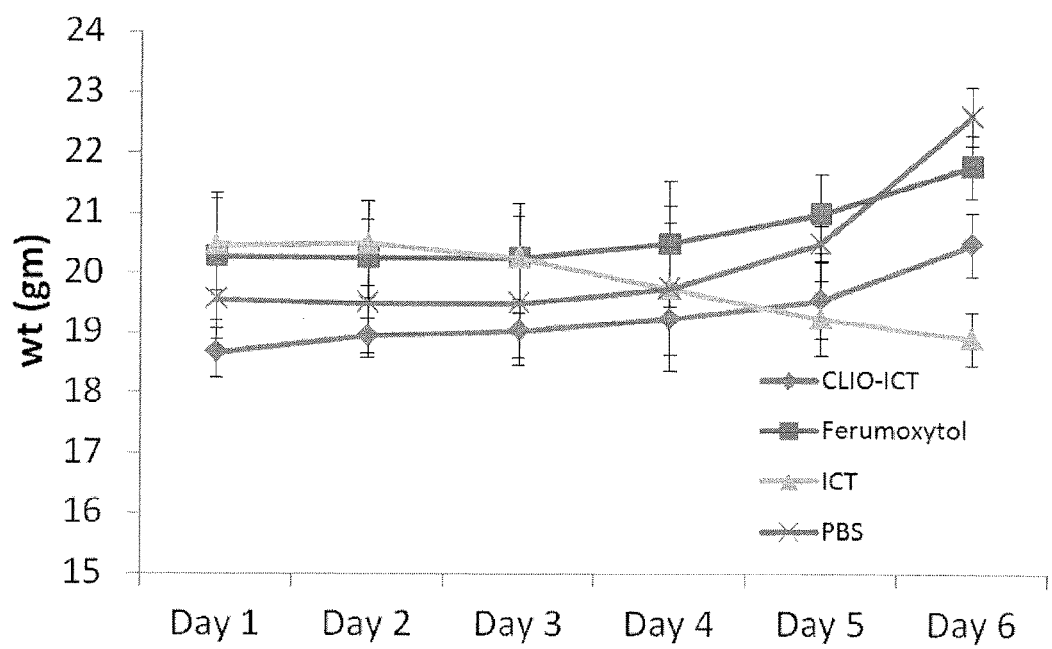

FIG. 10 shows average weight of tumours in grams. Tumour weight (gm) was monitored daily for 6 days after a single IV administration of CLIO-ICT, ferumoxytol, ICT, or PB5 (n 4 in each group).

Figure 11:
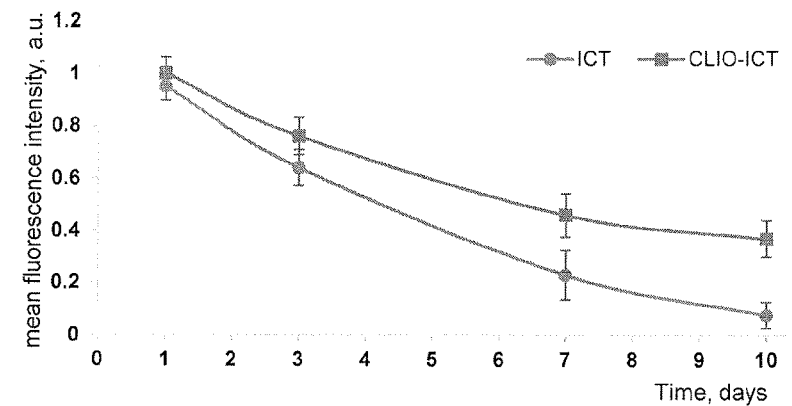

FIG. 11 shows the retention of ICT and CLIO-ICT in tumor following in vivo administration. The retention of ICT and CLIO-ICT was detected by fluorescence detection (521 nm) of the fluorescein endcap of the agents. The accumulation of these agents within the tumour is suggested to be a consequence of vascular collapse and their subsequent trapping in the tumour microenvironment, as previously reported by Atkinson et al. Fluorescence intensity was measured and averaged in six randomly selected areas of five slides from four mice in each group (120 measurements for each time point for each group).

Figure 12:
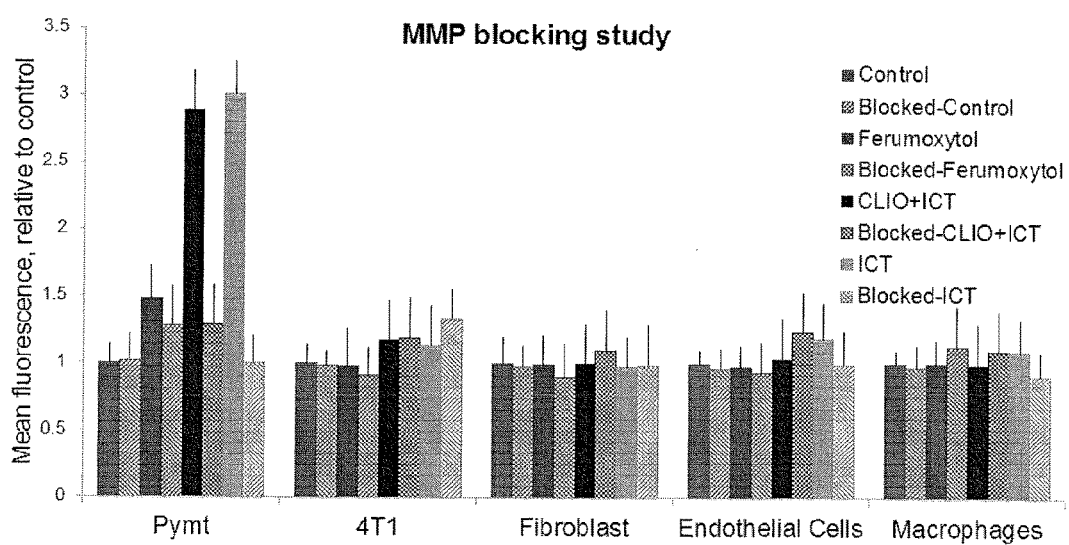

FIG. 12 shows prevention of cytotoxicity by CLIO-ICT and ICT in the presence of the MMP-selective inhibitor Ilomostat (GM-6001) as determined by evaluation of caspase activity. Cells (PyMT, 4T1, fibroblasts, endothelial cells and macrophages) were exposed for 4 hrs to CLIO-ICT, ICT, ferumoxytol only or solvent control in the presence or absence of Ilomostat. The cytotoxicity as displayed by mean fluorescence is diminished in the PyMT cells treated with CLIO-ICT and ICT blocked with Ilomostat. Graphs indicate expression of caspase, relative to control, and represent the mean of 3 independent experiments±standard deviation.

Figure 13:
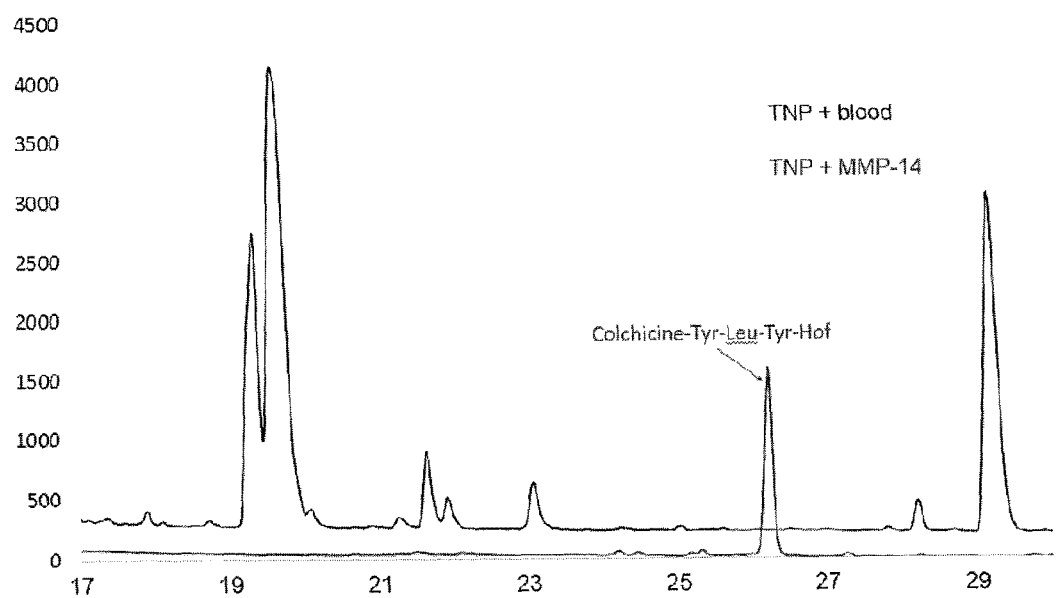

FIG. 13 shows an HPLC trace (detection at 320 nm) of TNP incubated with blood (upper line TNP+blood) and MMP-14 buffer (lower line TNP+MMP-14). To check TNPs off-site activation, both HPLC and LC-MS search for cleavage products including Colchicine-Tyr-Leu-Tyr-Hof (shown in FIG. 2C), Colchicine-Tyr-Leu-Tyr, Colchicine-Tyr-Leu, Colchicine-Tyr, and Colchicine, and their fragmentation products were performed. TNP incubated with blood didn't produce the Colchicine-Tyr-Leu-Tyr-Hof peak—one of the MMP-14 cleavage products. MS analysis of all other peaks did not reveal any matches with the potential cleavage products.

EXEMPLIFICATION

The theranostic strategy of the present invention builds on the previous development of ICT 2588 a novel MMP-14 activated tumour-targeted VDA which shows tumour selective activation and significant therapeutic efficacy with demonstrated potential for circumventing systemic toxicity. The conjugate of the present invention progresses and advances this strategy by linking this concept to a magnetic nanoparticle to create the theranostic conjugate CLIO-ICT described below.

1. Experimental Details
1.1 Synthesis of Theranostic Nanoparticles TNPs

For the synthesis of TNPs, we used the ultrasmall superparamagnetic iron oxide nanoparticle compound (USPIO) ferumoxytol, an FDA-approved iron supplement for intravenous treatment of iron deficiency. Ferumoxytol consists of an iron oxide core and a carboxymethyldextran coating. The carboxydextran coated ferumoxytol nanoparticles were first cross-linked with epichlorohydrin for better stability in vivo as described previously. Dialysis to remove low molecular weight compounds against water using dialysis tubing (12-14K cut-off) over three days yielded cross-linked iron oxide nanoparticles (CLIO). The obtained amine-presenting nanoparticles were then reacted (FIG. 1B) with the bifunctional linker, succinimidyl-([N-maleimidopropionamido]-4ethyleneglycol) ester (NHS-PEG$_4$-maleimide or SM (PEG)$_4$) in PBS (pH 7.4 buffer). Purification with Microcon® centrifuge filters (10 KDa cut-off, 5 mL ->0.2 mL volume reduction, 4600 rpm, PBS buffer addition and centrifugation was repeated 5 times) removed low molecular weight compounds to afford cross-linked iron oxide nanoparticles conjugated with the linker-bearing maleimide (CLIO-M).

MMP-14 activatable TNPs were synthesized by conjugating CLIO-M to the MMP cleavable peptide-conjugated azademethylcolchicine (ICT). ICT is a modified analogue of the previously reported ICT2588 (currently being progressed towards clinical trials) with an additional cysteine residue at the P5 position to allow conjugation to the nanoparticle via maleimide (FIG. 1). ICT was synthesized using a combination of solution and solid phase peptide synthesis methodologies, and purified by preparative HPLC as previously described. A fully side chain-protected molecule was prepared (ICT3104), to allow convenient storage, transport and to minimize potential cysteine-sulfur oxidation. Synthesis of side-chain protected peptide-conjugate intermediate: ICT3104 was produced by suspending the complete chlorotrityl chloride resin-immobilized peptide (250 mg) in a 1% solution of trifluoroacetic acid (TFA) in dichloromethane (4 mL). The suspension was agitated for 2 minutes, after which the solution was filtered under gravity directly into a 10% solution of pyridine in methanol (0.8 mL). This process of agitation in acid, followed by filtration and neutralization was repeated 10 times. Finally the resin was washed sequentially with dichloromethane (12 mL×3) and methanol (12 mL×3). This was repeated. Fractions containing the product were combined and evaporated to approximately 5% initial volume. Water was added at 0° C. to precipitate the crude product, which was subsequently purified by RP-HPLC using methodology previously outlined. Side-chain protecting groups were subsequently removed by dissolving ICT3104 (25 mg) in a mixture of TFA: triisopropylsilane (TIS): water (95:2.5:2.5, 1 mL) and stirring at room temperature for 2.5 hours. Following deprotection of ICT3104, the target agent ICT was precipitated with cold diethyl ether (40 mL), centrifuged, resuspended and washed twice with diethyl ether (40 mL). This procedure produced ICT in high yield and purity (13 mg, 91%). Excess of ICT (7 mg/mL, 50:1 molar ratio ICT: CLIO-M nanoparticle) was coupled with CLIO-M in PBS pH 7.4 buffer at room temperature. Purification with Microcon® centrifuge filters (10K cut-off, 5 mL ->0.2 mL volume reduction, 4600 rpm, PBS buffer addition and centrifugation) was repeated 10 times until the filtrate had no fluorescence to afford a purified construct, CLIO-ICT.

1.2 Physicochemical Characterization of TNPs

The iron concentrations of all nanoparticle samples were determined by Inductively Coupled Plasma Mass-Spectrometry (ICP-MS) on a Thermo Scientific XSERIES 2 View Spectrometer. The molar concentration of ferumoxytol was calculated using the concentration of iron determined by ICP-MS and known size of iron oxide core of a NP (6.5 nm on average by TEM≈3600 iron atoms as computed using Diamond® crystal structure analysis software). The amount of drug (ICT) covalently linked to a nanoparticle was calculated using two methods. In the first method, FITC (FITC:ICT=1:1, Table 1 below) concentration was determined by subtracting the maximum absorption (492 nm) of CLIO-ICT from the absorbance of unconjugated TNP alone (measured for CLIO-NH$_2$ at the same concentration of iron) and dividing the result by known extinction coefficient of FITC (70,000 M$^{-1}$ cm$^{-1}$) at 492 nm. In the second method, the FITC's emission peak of a diluted (to avoid fluorescence self-quenching) CLIO-ICT was integrated and its concentration was estimated using a calibration plot obtained for a set of standard FITC solutions. Both methods gave consistent results (less than 8% difference) for three different solutions of CLIO-ICT. TEM samples were prepared by drying 5 µL of 0.3 mM solution on carbon coated 600 mesh copper grid. The samples were imaged on a FEI Tecnai G2 F20 X-TWIN Transmission Electron Microscope at 200 kV accelerating voltage. Relativities ($r_1$ and $r_2$) were determined by measuring T1 and T2 relaxation times for a series of solutions with iron concentration of 1-60 mM on a Varian Inova 300 MHz (7 Tesla) NMR spectrometer using a series spin-echo and inversion recovery pulse sequences.

Dynamic Light Scattering (DLS, measures the hydrodynamic radius of the TNP) and Laser Doppler Electrophoresis (measures zeta potential) were performed on a Brookhaven 90 Plus Nanoparticle Size Analyser. The solutions of nanoparticles in the PBS buffer were filtered via Whatman GD/X 13 Syringe Filter (nylon, 0.2 µm) immediately before measurements. Dilution to 0.6 mM (iron) was required to obtain sufficient number of counts per second due to high value of absorption of TNPs. Absorption spectra were measured in a 1 cm path length cuvette using an Agilent 8453 absorption spectrophotometer. MALDI-MS spectrometric analyses were performed at the Mass Spectrometry Facility of Stanford University. HPLC was performed on a Dionex HPLC System (Dionex Corporation) equipped with a GP50 gradient pump and an inline diode array UV-Vis detector. A reversed-phase C18 (Phenomenax, 5 μm, 10×250 mm or Dionex, 5 μm, 4.6×250 mm) column was used with a MeCN (B)/H$_2$O (A) gradient mobile phase containing 0.1% trifluoroacetic acid at a flow of 3 or 1 mL/min for the analysis.

TABLE 1

Theranostic Nanoparticles characterization summary

| | D, nm (DLS) | Z, meV | # of ICT | $r_1/r_2$, 1/mMol * s |
|---|---|---|---|---|
| Ferumoxytol | 19 ± 4 | −13 ± 5 | | 32.3/74.9 |
| CLIO-ICT | 21 ± 3 | +21 ± 7 | 4.7 ± 0.4 | 38.9/56.0 |
| CLIO-ICT cleaved | 19 ± 4 | +16 ± 6 | 0.6 ± 0.2 | 39.5/55.8 |

1.3 In Vitro Studies

The murine breast carcinoma MMTV-PyMT (isolated from MMTV-PyMT mouse breast tumours) and 4T1 (ATCC CRL-2539) cell lines, and human dermal fibroblasts (ATCC PCS-201-012) were obtained from the American Type Culture Collection and authenticated both morphologically and by short tandem repeat analysis. Cell lines were cultured as monolayers in RPMI 1640 supplemented with 10% (v/v) foetal bovine serum, sodium pyruvate (1 mM), and L-glutamine (2 mM). All cell lines were used at a low passage in our laboratory for a maximum of 6 months post-resuscitation and were tested regularly to confirm lack of Mycoplasma infection.

Assessment of MMP-14 gene expression of MMTV-PyMT and 4T1 tumour cells as well as human dermal fibroblasts as controls was determined by qPCR. qPCR expression analysis for MMP-14 and the control marker GAPDH was done and the total cellular RNA was extracted from each sample with the QIAGEN RNeasy® mini kit. cDNA was prepared from total RNA and quantitative real-time PCRs (qPCRs) were carried out and analyzed on an Applied Biosystems StepOne™ Real-Time PCR System. The formation of double-stranded DNA product was monitored by TaqMan® gene expression primers.

To monitor stability of CLIO-ICT and ICT, 2 mL of PyMT mouse blood was collected and 100 μL of 0.4 M (Fe) solution of CLIO-ICT and 100 μL 0.29 mM solution of ICT were incubated with 500 μL of fresh blood each at 37° C. for three days. The solutions were filtered via Whatman GD/X 13 Syringe Filter (nylon, 0.2 μm) and analysed by MALDI Mass-Spectrometry.

Subsequently, triplicate samples of MMTV-PyMT tumour cells and human dermal fibroblasts were incubated with ferumoxytol, CLIO-ICT, ICT, or PBS, and analysed for caspase-3 activity levels, a marker of cytotoxicity using the SensoLyte® Homogeneous AMC Caspase-3/7 assay kit (AnaSpec, Inc., California), according to the manufacturer's instructions. Release of the AMC fluorophore following cleavage of the specific fluorometric caspase substrate, DEVD-AMC was detected using a fluorometer (ex/em=354 nm/442 nm).

1.4 In Vitro Viability Studies Using MTT Assay

The selective cytotoxicity of CLIO-ICT and ICT against MMP-14 expressing cell types was assessed using the MMT assay following 96 hr in vitro exposure of the cell types to CLIO-ICT, ICT, Ferumoxytol or 0.1% DMSO (Control). The cell types were PyMT, 4T1, fibroblasts, endothelial cells and macrophages. Both PyMT and 4T1 demonstrate sensitivity to the MMP-14-activated agents, CLIO-ICT and ICT, whilst MMP-14-negative forblasts, endothelial cells and macrophages did not. No toxicity was observed when cells were exposed to ferumoxytol alone. FIG. 8 shows the mean of 3 independent experiments±standard deviation 1.5 In Vivo Evaluation of Theranostic Activity All procedures were approved by the animal care and use committee at Stanford University. MMTV-PyMT mice that spontaneously develop multifocal, multiclonal mammary adenocarcinomas were used. Explants of MMTV-PymT tumours were implanted into 24 four week old female FvBN mice as described previously. When the tumours had reached a size of 1 cm, four groups of six mice each received a single intravenous injections of 0.6 M (Fe) solution of ferumoxytol (0.5 mmol Fe/kg), 0.4 M (Fe) solution of CLIO-ICT (0.75 mmol Fe/kg and 1 μmol/kg of ICT), 0.29 mM solution of ICT (1 μmol/kg), or PBS (1.0 μl/gm). Due to the approximately 1/3 lower r2-relaxivity of the TNPs compared to the original ferumoxytol, TNPs were administered at a correspondingly higher iron oxide dose. All mice underwent MR imaging on a 1 T desktop MR scanner (Aspect M2™ Compact High Performance MR System, Toronto, ON). Animals were anesthetized with isofluorane and placed in a dedicated radiofrequency coil for high resolution MR imaging, using T2-weighted SE sequences (TR 2500 ms, TE 20, 40, 60, 80 ms) with a field of view (FOV) of 6×6 cm (1T), a matrix of 128×128 pixels and a slice thickness of 1-2 mm. MR scans were obtained directly before, continuously up to 1 hour (h) post injection (p.i.) of ferumoxytol, CLIO-ICT, ICT or PBS, as well as 24 h p.i. T2-relaxation times of the tumour were calculated based on multiecho SE sequences and converted to R2-relaxation rates (R2=1/T2), which are proportional to contrast agent concentration. The relative change in R2 data between pre- and postcontrast MR scans, ΔR2(%) was determined as a quantitative measurement of tumour contrast enhancement.

1.6 Antitumour Activity

Mice bearing subcutaneous PyMT tumours were randomized into groups (n=6 mice) and received either ferumoxytol, CLIO-ICT, or ICT via intravenous administration. Tumour size (measured by calipers) was recorded daily for 7 days. Tumour diameter and volumes were recorded. Tumour volume was calculated using the formula: $(a^2 \times b)/2$ (a and b are the smaller and larger dimension of the tumour, respectively).

1.7 Histological Assessment of TNPs and Caspase-3 Activity

The distribution of nanoparticles and induction of caspase-3 activity was assessed 48 hours following intravenous administration of TNP and drugs. Mammary tumours and samples of visceral organs were explanted, and placed in Optimal Cutting Temperature (OCT) compound on dry ice for histological processing. For detection of FITC-labelled nanoparticles and therapeutic drugs all slides were mounted using ProLong Gold with DAPI (Invitrogen) and analysed using an LSM510 confocal microscope (Zeiss, Thornwood, N.Y.). Histologic sections of mammary tumours and visceral organs were stained using standard H&E and iron was detected using DAB-enhanced Prussian Blue staining. Caspase-3 activity was evaluated immunohistochemically by antibody staining of cleaved caspase-3 (Cell Signalling Technology 9661) and Cy3-labelled biotin/avidin detection (Vector Labs and Jackson ImmunoResearch). Labelled cells were analysed by fluorescence microscopy.

1.8 Statistical Analyses

Quantitative data of experimental groups receiving different diagnostic or therapeutic agents were compared with a Wilcoxon rank sum test and an analysis of variance. P<0.05 was considered significant.

Results 2.1 Design of MMP activatable conjugate

The concept for the MMP activatable conjugates of the present invention is shown in FIG. 1, and the conjugates comprise:
i. Nanoparticle bearing a MRI contrast agent,
ii. MMP cleavable peptide, and
iii. A vascular disrupting agent (VDA).

These TNPs are comprised of the following: (i) the nanoparticle bearing a MRI contrast agent is a cross-linked iron oxide (CLIO) nanoparticle with an ultra-small (6.5 nm) iron oxide crystal encapsulated into an 8 nm thick polysaccharide dextran shell. Superparamagnetism of the core allows for MR imaging of the TNP. (ii) The MMP cleavable peptide is an MMP-14 peptide recognition sequence with an N-terminal masking group containing fluorescein: FITC-βAla-Cys-Arg-Ser-Cit-Gly-Hof-Tyr-Leu-Tyr (SEQ ID NO: 11) that is specifically cleaved between glycine and homophenylalanine (Hof) by tumour-associated MMP-14. (iii) The VDA is azademethylcolchicine. The amino group of azademethylcolchicine was attached to the peptide, thereby rendering the drug non-toxic until activated, as demonstrated previously for the MMP-activated prodrug ICT2588. The fluorescent masking group enables physicochemical characterization and therefore serves as a label for TNPs, in addition to its role in providing metabolic stability to the peptide.

2.2 Physicochemical Properties of TNPs

CLIO-ICT was characterized by Dynamic Light Scattering (DLS), Laser Doppler Electrophoresis, UV-Vis absorption spectroscopy, fluorescence spectroscopy, and Nuclear Magnetic Resonance (Table 1). DLS measurements showed the expected increase in the NPs size from 19 nm to 21 nm after conjugation with ICT. Cross-linking, amine group addition, and ICT attachment also changed the charge of the nanoparticle: it was negative for ferumoxytol, positive for both CLIO-ICT and its MMP-14 cleavage product according to laser Doppler electrophoresis (zeta potential measurements, Table 1). The number of ICT molecules per iron oxide nanoparticle was determined to be on average 4.7 from the attached fluorescein absorption and known TNP concentration.

Figure 2:
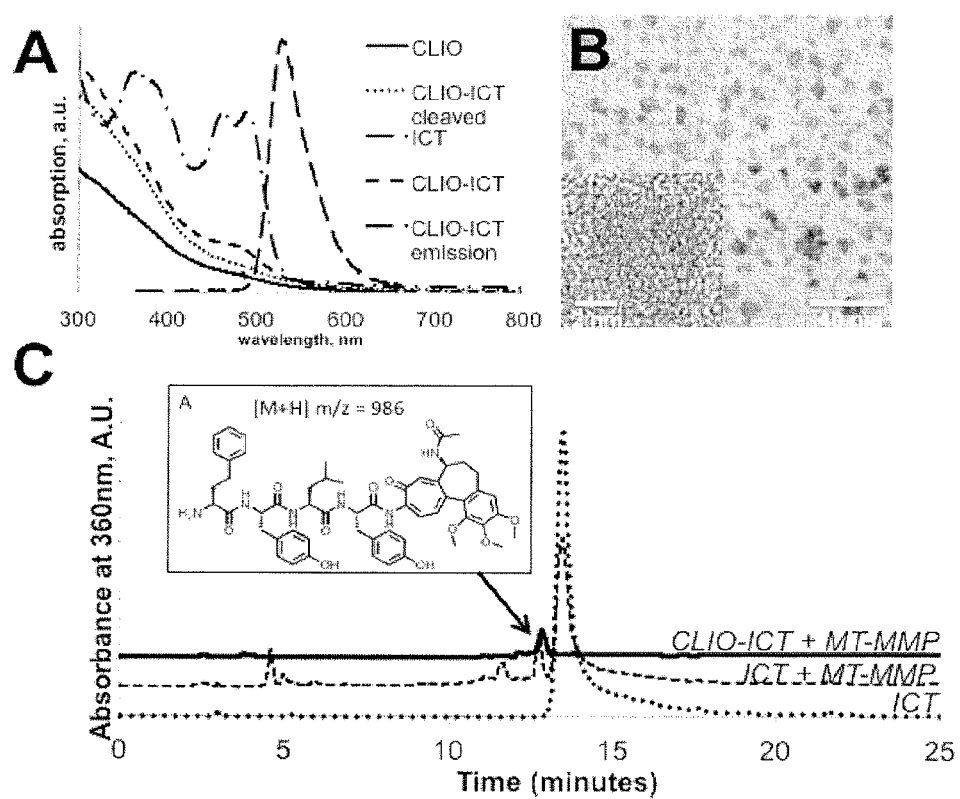
FIG. 2 (A) shows absorption spectra of the TNPs and their components (a.u.=arbitrary units)

TNP activation was studied using HPLC to analyse solutions of both ICT (10 mM) and CLIO-ICT (10 mM) post-incubation with recombinant MMP-14 (20 μg/mL) in PBS buffer at 37° C. (FIG. 2). One of the major peptide metabolites identified by mass spectrometry (HPhe-Tyr-Leu-Tyr-azademethylcolchicine) was identical to the one previously reported for the original ICT2588 prodrug, confirming that the two molecules have similar cleavage profiles. It was previously shown that this cleavage fragment is subsequently metabolized rapidly in the tumour by exopeptidases in a non-specific manner to release the active drug. The chosen length of the linker (2.6 nm, calculated in Chem3D Ultra 8.0) was sufficient for efficient cleavage: MMP-14 cleaved the peptide linker and released 87% of the total calculated quantity of ICT after 2 hours as measured by absorption spectra (almost no characteristic absorption of ICT in absorption spectra after cleavage). MMP-14 treatment of ICT in identical conditions cleaved 89% of the prodrug as was observed by HPLC assays.

The size of the TNPs decreased slightly upon cleavage by MMP-14 as measured by DLS (Table 1). As expected, the iron oxide core size did not change upon functionalization (6.5±0.7 after functionalization versus 6.2-7.3 before) as determined by Transmission Electron Microscopy (TEM; Table 1). Modified TNPs had slightly higher r1's (38.9 for CLIO-ICT and 39.5 mM$^{-1}$s$^{-1}$ for the cleaved CLIO-ICT) and lower r2's (56.0 for CLIO-ICT and 55.8 mM$^{-1}$s$^{-1}$ for the cleaved CLIO-ICT) compared to original ferumoxytol nanoparticles (32.3 and 74.9 mM$^{1}$s$^{-1}$, respectively), which is likely due to the increase in molecular weight and the nature of the coating.

2.3 Anticancer Activity of TNPs In Vitro qPCR revealed significant MMP-14 expression in MMTV-PyMT tumour cells, while 4T1 tumour cells and fibroblasts did not show significant MMP-14 expression (FIG. 3B). Expression data were collected as Ct values and the gene expression levels were normalized to the reference control gene, GAPDH. MMTV-PyMT tumour cells showed significant cell death after incubation with CLIO-ICT (caspase expression ratio of 2.883:1 relative to the PBS control) and ICT (caspase expression ration of 2.994:1 relative to the PBS control), but not after incubation with ferumoxytol (1.47:1) and PBS control (1:1). 4T1 cells were not responsive to treatment with CLIO-ICT and MMP-14 negative fibroblasts did not show any significant cytotoxic effects after incubation with CLIO-ICT or ICT (FIG. 3A).

In addition we found that activation of the drug is in fact due to MMP-14 dependent cleavage of the probe be performing a set of MMP blocking experiments with Ilomostat which showed disappearance of CLIO-ICT and ICT antitumour activities (FIG. 12).

2.4 Tumour Accumulation of TNP In Vivo

Figure 4:
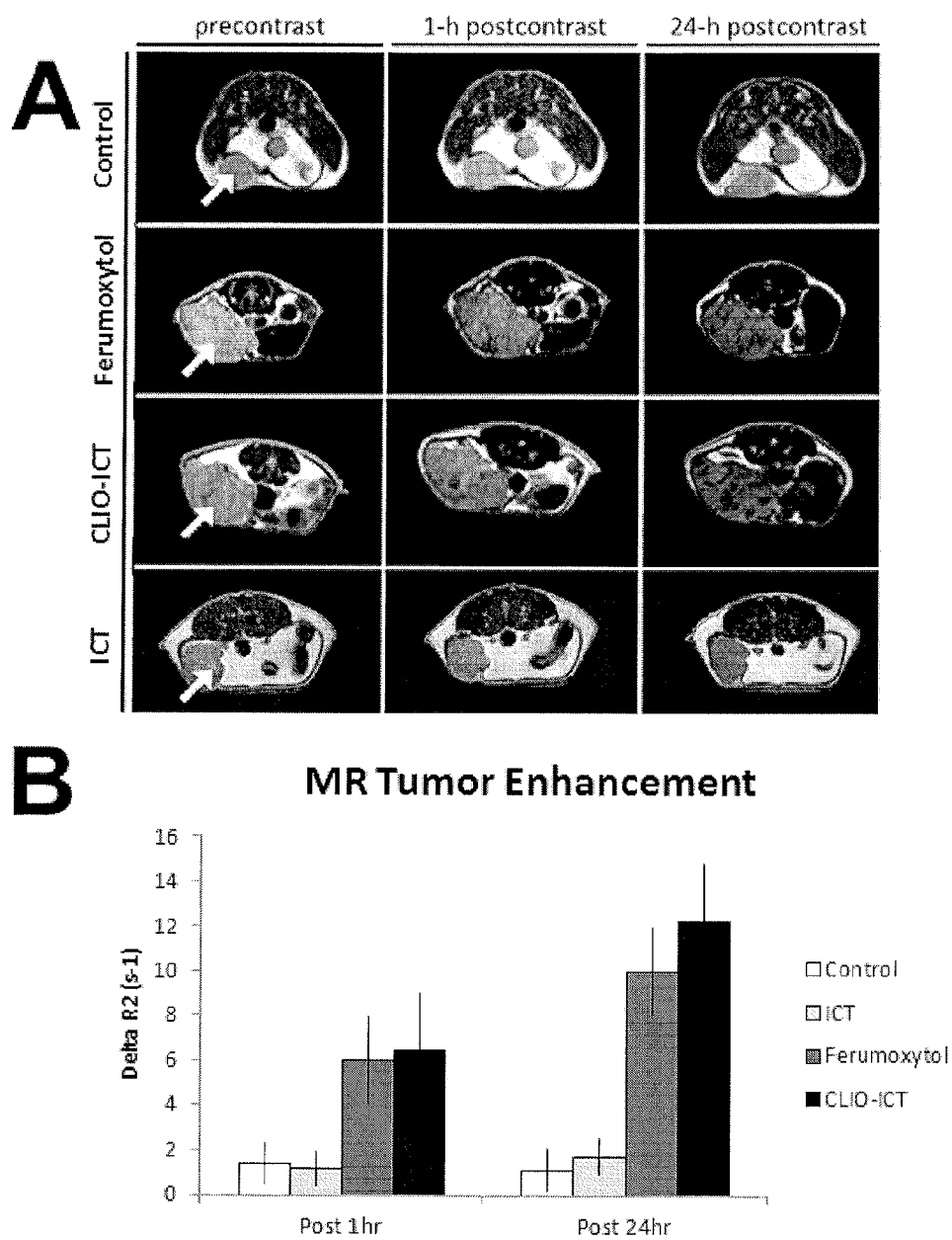
FIG. 4 (A) shows axial T2-weighted MR images (TR 2500 ms, TE 80 ms) of MMTV-PyMT mammary tumours before and after a single intravenous injection: 0.6 M (Fe) solution of ferumoxytol (0.5 mmol Fe/kg), 0.4 M (Fe) solution of CLIO-ICT (0.75 mmol Fe/kg and 1.0 µmol/kg of ICT), 0.29 mM solution of ICT (1.0 µmol/kg), or PBS (1.0 µl/µm). Contrast agent accumulation is noted as a negative (dark) signal enhancement of the tumours.

After a single intravenous injection of ferumoxytol (0.5 mmol Fe/kg) and CLIO-ICT (0.75 mmol Fe/kg), MMTV-PyMT tumours demonstrated a negative (dark) enhancement on postcontrast T2-weighted MR images (FIG. 4). This negative tumour enhancement persisted for the entire time period of observation, up to 24 h post-injection. Tumour enhancement with TNPs was not significantly different compared to the tumour enhancement with the original, "diagnostic" nanoparticle ferumoxytol (FIG. 4). Control mice injected with the therapeutic ICT or injected with PBS did not show any significant MR signal enhancement (FIG. 4). This result confirmed that the evaluated MMTV-PyMT tumours did not exhibit any intrinsic changes in MR signal within a two-day observation period and that ICT did not cause any MR signal changes either. Detection of iron using DAB-enhanced Prussian Blue staining and immunostaining of TNP-FITC with Alexa 488 conjugated anti-FITC antibody confirmed accumulation of TNPs and ferumoxytol in MMTV-PyMT tumours (FIG. 5). Accumulation of TNPs in the tumour was also monitored by measuring the fluorescence of fluorescein which is the part of both CLIO-ICT and ICT. TNP showed higher fluorescence intensity in the tumour at all times which is likely to be due to a higher accumulation of CLIO-ICT relative to ICT (FIG. 11).

2.5 Antitumour Activity of TNPs In Vivo

Figure 3:
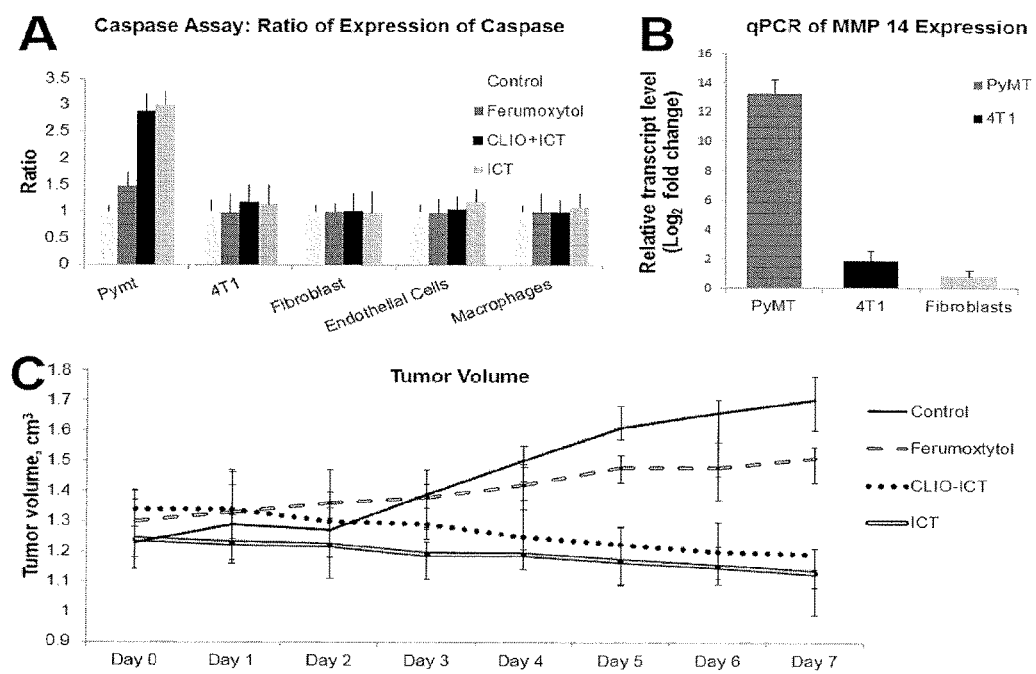
FIG. 3 (A) shows results of a caspase assay: PyMT, 4T1, human dermal fibroblasts, endothelial cells, and macrophages were incubated with PBS, Ferumoxytol only, CLIO-ICT, and ICT only. After incubation the assay was run for 4 hr—readings taken every 5 min. Cells incubated with CLIO-ICT along with those incubated with ICT showed more fluorescence (more cell death) than those incubated with ferumoxytol only and PBS only. Cells incubated with ICT only showed similar levels of fluorescence but showed a plateau after 60 min.

Daily monitoring of MMTV-PyMT tumour size indicated that PBS and ferumoxytol treated subjects showed an increase in tumour size (P=0.002) whereas those treated with CLIO-ICT and ICT showed an overall decrease in tumour size (P=0.003; FIG. 3). Pathologic evaluation of tumours confirmed a progressive increase in the severity of tumour necrosis following ICT or CLIO-ICT treatment (FIG. 5). In contrast, no significant tumour necrosis was observed in ferumoxytol treated tumours (FIG. 5). An analogous pattern of progressive cellular cytotoxicity was observed with the Cy3-labeled cleaved Caspase-3 immunofluorescent staining: there was rare labelling of tumour cells for the ferumoxytol injected mice, but significant labelling of tumour cells from both the ICT and CLIO-ICT treated mice (FIG. 5). Iron deposits were noted within ferumoxytol and CLIO-ICT treated groups, but not in PBS or ICT-treated groups (FIG. 5).

Conversely, no significant toxicity was observed in normal organs (liver, spleen, kidney, brain, bone marrow and heart), detected either histologically, by detection of caspase-3 activity (FIG. 6), and animal weight loss (FIG. 10). In addition we monitored the stability of CLIO-ICT and ICT in mouse blood plasma and found no ICT cleavage products by mass-spectrometry.

CONCLUSIONS

As demonstrated above the conjugate of the present invention illustrated by CLIO-ICT provides the opportunity to monitor and potentially enhance therapeutic efficacy, with the key advances being the ability to identify tumour localization and disease extent, and simultaneously evaluate and quantify the in vivo tumour accumulation of the therapeutic with MR imaging.

We showed MMP-14 hydrolysis of CLIO-ICT to liberate the correct proteolytic-VDA fragment through cleavage at the glycine-homophenylalanine bond, and differential in vitro chemosensitivity in MMTV-PyMT (high MMP-14) but not in 4T1 (low MMP-14) tumour cells or normal fibroblasts. In addition, the systemic stability of CLIO-ICT and tumour-selective delivery is reinforced by MRI detectable tumour-enhancement, a non-invasive observation not possible with ICT which is not bound to an imaging NP.

Conjugation of ICT to the NP did not diminish the anticancer efficacy of the prodrug as significant haemorrhagic necrosis was observed in the tumour following administration. This mechanism is consistent with VDA-induced decrease in functional tumour vasculature, a pharmacodynamic effect observed for ICT2588 and other VDA approaches. Additionally, no antitumour effect or tumour response was observed in the ferumoxytol (NP) treated mice, which supports the fact that the therapeutic effect is derived directly from the released VDA entity. Most importantly for this approach and as suggested by the previous study with ICT2588, there was a lack of detectable toxicity and MR signal in non-tumour tissues, strongly supporting the tumour-selective toxicity and widespread potential of this strategy.

CLIO-ICT demonstrated both significant MR imaging effects and anticancer activity, with selective and effective delivery to the tumour site, and with consecutive reduction of associated toxicity-liability to normal organs. In addition, the conjugation of a therapeutic to nanoparticles allows for a significantly higher drug payload to be delivered. The advantages of our CLIO-ICT nanotherapeutics include the ability to track the drug with MRI, together with longer retention in the tumour tissue via VDA-initiated vascular collapse and drug entrapment, and improved antitumour efficacy. Conceptually this is important, as by noninvasively visualizing how well our TNP accumulates at the target site, patient response to TNP treatment may be preselected. Furthermore, this TNP approach also allows longitudinal monitoring of patient response, allowing drug doses and treatment protocols to be individualized and optimized during follow-up. Consequently, the TNP approach holds significant potential for improving the targeted therapy of cancers, and personalized nanomedicine-based chemotherapeutic interventions, to achieve delivery of the right drug to the right location in the right patient at the right time.

The invention claimed is:

1. A matrix metalloprotease (MMP) activatable conjugate lacking folate and comprising:
   a vascular disrupting agent (VDA) which binds to the colchicine binding site of tubulin and wherein the VDA is selected from the group consisting of azademethylcolchicine, azacolchicine, N-methyl desacetylcolchicine, desacetylcolchicine and N-acetylcolchinol-O-phosphate,
   a MMP cleavable peptide comprising the amino acid sequence -Gly-Hof-Tyr-Leu- (SEQ ID NO: 1) or -Arg-Ser-Cit-Gly-Hof-Tyr- (SEQ ID NO: 2), and
   a nanoparticle comprising a magnetic resonance imaging (MRI) contrast agent, the MRI contrast agent comprising an ion selected from the group consisting of gadolinium, iron, platinum, manganese, copper, gold and barium.

2. A conjugate according to claim 1 wherein the MMP cleavable peptide comprises the amino acid sequence -Gly-Hof-Tyr-Leu- (SEQ ID NO: 1).

3. A conjugate according to claim 1 or 2, wherein the MMP cleavable peptide further comprises a -Cys- at the N- or C-terminus of SEQ ID NO:1 or SEQ ID NO: 2.

4. A conjugate according to claim 1, wherein the nanoparticle is from 3 to 200 nanometers (nm) in diameter.

5. A conjugate according to claim 1, wherein the MRI contrast agent comprises an iron ion and is selected from the group consisting of iron oxides, magnetite ($Fe_3O_4$) and maghemite ($Fe_2O_3$).

6. A conjugate according to claim 5, wherein the iron oxide is superparamagnetic iron oxide (SPIO) or ultrasmall superparamagnetic iron oxide (USPIO).

7. A conjugate according to claim 5, wherein the MRI contrast agent is a carbohydrate coated iron oxide particle.

8. A conjugate according to claim 1, wherein the VDA is azademethylcolchicine.

9. A matrix metalloprotease 14 (MMP-14) activatable conjugate lacking folate and comprising:
   a VDA which binds to the colchicine binding site of tubulin, and wherein the VDA is selected from the group consisting of Azademethylcolchicine, Azacolchicine, N-methyl desacetylcolchicine, Desacetylcolchicine and N-acetylcolchinol-O-phosphate,
   a MMP-14 cleavable peptide comprising the amino acid sequence -Arg-Ser-Cit-Gly-Hof-Tyr-Leu- (SEQ ID NO: 6), and
   a nanoparticle of 3 to 200 nm in diameter comprising a magnetic resonance imaging (MRI) contrast agent, the MRI contrast agent comprising an ion selected from gadolinium, iron, platinum, manganese, copper, gold or barium.

10. A pharmaceutical composition comprising the conjugate of claim 1 or 9, and a pharmaceutically acceptable carrier, vehicle, diluent or excipient.

11. A method for treating a tumour comprising administering to a subject in need thereof an effective amount of the conjugate of claim 1 or 9.

12. A method for treating and imaging a tumour comprising administering to a subject in need thereof an effective amount of the conjugate of claim 1 or 9, the method further comprising obtaining an MRI image of the subject's tumour site.

13. A method for treating a tumour and monitoring VDA delivery to the tumour in a subject, the method comprising administering the conjugate of claim 1 or 9 to a subject in need thereof and obtaining one or more MRI images of the subject's tumour site.

14. A method according to claim 13, wherein a first MRI image of the tumour site is obtained at a first point in time and a second MRI image of the tumour site is obtained at a subsequent second point in time, thereby enabling VDA delivery to the tumour site to be monitored.

15. The conjugate of claim 2, wherein the MMP cleavable peptide comprises an amino acid sequence selected from the group consisting of -Ser-Cit-Gly-Hof-Tyr-Leu- (SEQ ID: 4), -Arg-Ser-Cit-Gly-Hof-Tyr-Leu- (SEQ ID NO: 6), -βAla-Arg-Ser-Cit-Gly-Hof-Tyr-Leu- (SEQ ID NO: 9) and -βAla-Arg-Ser-Cit-Gly-Hof-Tyr-Leu-Tyr- (SEQ ID NO: 10).

16. The conjugate of claim 7, wherein the iron oxide particle is coated with dextran.

17. The conjugate of claim 7, wherein the iron oxide particle is ferumoxytol.

18. The conjugate of claim 9, wherein the MMP cleavable peptide further comprises a -Cys- at the N- or C-terminus of SEQ ID NO:6.

* * * * *